United States Patent
Batiste (10) Patent No.: US 9,387,062 B2
(45) Date of Patent: Jul. 12, 2016

(54) INTRAVENOUS DEEP VEIN THROMBOSIS FILTER AND METHOD OF FILTER PLACEMENT

(76) Inventor: Stanley Batiste, Las Vegas, NV (US)

(*) Notice: Subject to any disclaimer, the term of this patent is extended or adjusted under 35 U.S.C. 154(b) by 2405 days.

(21) Appl. No.: 12/012,136

(22) Filed: Jan. 30, 2008

(65) Prior Publication Data

US 2008/0183206 A1    Jul. 31, 2008

Related U.S. Application Data

(60) Provisional application No. 60/898,939, filed on Jan. 31, 2007.

(51) Int. Cl.
*A61M 29/00* (2006.01)
*A61F 2/01* (2006.01)

(52) U.S. Cl.
CPC .............. *A61F 2/01* (2013.01); *A61F 2002/011* (2013.01); *A61F 2002/016* (2013.01); *A61F 2230/0006* (2013.01); *A61F 2230/0091* (2013.01); *A61F 2250/0059* (2013.01)

(58) Field of Classification Search
CPC ................ A61F 2/01; A61F 2002/016; A61F 2002/011; A61F 2230/0091; A61F 2230/0006; A61F 2250/0059; A61B 17/12022; A61B 17/12109
USPC ........................................................ 606/200
See application file for complete search history.

(56) References Cited

U.S. PATENT DOCUMENTS

| | | | | | |
|---|---|---|---|---|---|
| 3,840,017 | A | * | 10/1974 | Violante | 606/146 |
| 5,188,616 | A | * | 2/1993 | Nadal | 604/218 |
| 6,059,825 | A | * | 5/2000 | Hobbs | A61F 2/01 623/1.18 |
| 2002/0010481 | A1 | * | 1/2002 | Jayaraman | A61B 17/0057 606/151 |
| 2004/0034383 | A1 | * | 2/2004 | Belson | A61M 25/0054 606/191 |
| 2006/0212127 | A1 | * | 9/2006 | Karabey | A61B 17/12031 623/23.75 |
| 2006/0229668 | A1 | * | 10/2006 | Prestezog et al. | 606/213 |

* cited by examiner

*Primary Examiner* — Tuan V Nguyen
*Assistant Examiner* — Kevin Everage
(74) *Attorney, Agent, or Firm* — Weide & Miller, Ltd.

(57) ABSTRACT

A vascular filter system and method are disclosed. In one embodiment, the filter system comprises a dispensing needle releasably attached to a filter dispenser which stores a length of filter wire. The filter wire dispenser has a guide tube which guides the filter wire into the needle and then into a vein during surgical implantation. The filter wire is configured to coil into a predetermined shape as it is deployed from the needle. The shape of the filter wire captures blood clots in the blood stream. Once the filter wire is deployed, the needle may be removed and a portion of the filter wire may be left protruding from the patient's skin surface to allow the filter wire to be secured by a fixation device. A syringe may be used to draw blood to confirm that the needle is properly positioned within a vein before the filter wire is deployed.

10 Claims, 8 Drawing Sheets

INTRAVENOUS DEEP VEIN THROMBOSIS FILTER AND METHOD OF FILTER PLACEMENT

CROSS-REFERENCE TO RELATED APPLICATIONS

This application claims priority to U.S. Provisional Patent Application No. 60/898,939 filed on Jan. 31, 2007 titled IMPROVED INTRAVENOUS DEEP VEIN THROMBOSIS FILTER AND METHOD OF FILTER PLACEMENT.

BACKGROUND OF THE INVENTION

1. Field of the Invention

The present invention relates to vascular filters and, in particular to surgically implanted vascular filters which capture blood clots to prevent the clots from migrating to other regions of the circulatory system.

2. Related Art

Deep vein thrombosis (DVT) is a common problem and causes significant morbidity and mortality in the United States and throughout the world. DVT is caused when a blood clot forms in the deep veins of the legs. These blood clots typically occur due to slow or reduced blood flow through the deep veins such as when the patient cannot ambulate or otherwise efficiently circulate their blood. Another cause of inefficient circulation may be due to structural damage to the veins such as general trauma or subsequent to surgical procedures. Additionally, a blood clot may form in a deep vein due to a particular medical condition or a propensity for the patient to have a hypercoaguability state. For example, a woman on birth control who smokes has an increased risk of forming blood clots and is thus predisposed to DVT.

The result and clinical significance of DVT is when the clot breaks free from its location in the deep vein of the leg, the clot travels through the circulatory system and may eventually lodge in a location that is adverse to the patient's health. For example, the clot may dislodge from a location in the deep vein of the patient's leg and migrate through the heart and come to rest in the patient's lung causing a pulmonary embolism (PE) resulting in restricted circulation and can cause sudden death for the patient.

DVT & PE are currently prevented in several ways including anticoagulation therapy, thrombectomy, thrombolysis and inferior vena cava filter (IVC filter) placement. Anticoagulation therapy utilizes various medications that reduce the patient's propensity for forming blood clots. However, this form of therapy has the disadvantage that due to the patient's inability to form blood clots (due to the medication), there is an increased risk of excessive bleeding should the patient become injured, sustain surgical complications, or develop internal hemorrhaging.

Thrombectomy is a procedure generally performed for treatment of a PE, in which a blood clot is extracted from the vein using a surgical procedure or by way of an intravenous catheter and a mechanical suction device. This form of treatment is risky and technically very difficult because the catheter has to be steered or navigated to a specific location in order to extract the clot. Additionally, during a thrombectomy there is an increased risk of causing vascular damage due to the surgical procedure and use of various mechanical devices.

Thrombolysis is a medical technique that is performed for treatment of a PE, in which various medicines are infused into the region of the clot that subsequently causes the clot to dissolve. This form of treatment has the disadvantage that the medication may cause bleeding at other sites such as within the brain. For example, if a patient has previously had a minute non-clinical stroke, the medication used in a thrombolysis may cause a previously healed vessel to bleed within the patient's head. IVC filter placement is usually conducted by surgically installing a filter in a large bore vein (such as the inferior vena cava) in the patient's upper abdomen. The IVC filter is placed using a large bore catheter (Introducer Catheter) for delivery of the filter. There are a couple of filters frequently used, those that are permanent and those that are removable, that may be placed using this technique. In the case where a removable filter is utilized, additional complications arise when the filter must be removed. The removable IVC filter is generally placed for a time period of a several weeks to a few months to prevent internal vascular scaring. However, removal of the IVC filter is technically challenging and requires large bore access. In practice, the removable IVC filter is captured by first accessing a large bore vein, using a large bore catheter to approach the filter, capturing the tip of the filter using a "snaring device" that is deployed through the large bore catheter, then pulling the filter into the catheter, and then the large bore catheter (with the filter therein) is removed from the patient. This procedure is very challenging, and requires increased patient recovery time.

Current IVC filter placement has several disadvantages such as increased costs, requires the use of special surgical procedures such as fluoroscopy or cardiology labs, requires a team (lab technician, nurse, and physician) of medical professionals, and requires a second substantially difficult surgical procedure for filter removal. Additionally, the IVC filter placement procedure requires that the patient's coagulation status be sufficient to withstand the surgical procedure. For example, if the patient has medical condition (liver failure) or is on medications that prevents their blood from clotting (i.e., using anticoagulation therapy) there is a substantial risk of excessive bleeding during the procedure. Also, existing IVC filter placement procedures are of questionable practicality for preventative placement because of the intrusive surgical procedures that must be performed to place the filter. Correspondingly, the risks (particularly filter removal) must be balanced between the need for the filter and the patient's ability to endure the surgical procedure.

As a result, there is a need in the art for a vascular filter that is inexpensive, facilitates placement by a physician at a convenient patient location (bedside), allows non-intrusive removal that can be performed at any location by either a physician or trained technician while having minimal recovery time and eliminating the need to determine the coagulation status of the patient. The method and vascular filter described herein enables a physician to place and remove the filter with minimal physical intrusion and at the same time reducing risk of procedural complications for the patient.

SUMMARY OF THE INVENTION

To overcome the drawbacks of the prior art and provide additional benefits and features, a vascular filter and method of filter placement is disclosed. In one embodiment, the vascular filter includes a dispensing needle releasably attached to a syringe and a filter wire dispenser. Generally, the needle has two ends, a delivery end and a coupling end. The delivery end is placed within a vein and allows filter wire to be implanted into the vein. The coupling end allows the needle to be releasably connected to a filter wire dispenser or syringe.

The filter wire dispenser stores a length of filter wire which is configured to coil upon deployment from the delivery end of the needle into a vein. The filter wire dispenser may store the filter wire as a spool or linearly, and includes a guide tube sized to insert into the needle. The guide tube is used to guide the filter wire from the dispenser into the needle.

The filter wire may be configured to coil upon deployment in a number of ways. One way is to put residual stresses, surface tensions, or both into the filter wire such that, once deployed, the filter wire will coil into a predetermined shape as defined by the stresses and surface tensions in the filter wire. The filter wire may be configured to coil into a vortex type, nested, or tangled web shape as desired. In addition, the filter wire of some embodiments may have a flexible tip to better prevent damage to the interior walls of a vein.

Once deployed a portion of the filter wire may be left protruding from the patient to allow the filter to be fixed in position. The protruding portion of the filter wire may be secured to a fixation device attached to the patient's skin. In one or more embodiments, the fixation device may have a portion configured to engage and secure the filter wire such as a protrusion.

The vascular filter, in one embodiment, is implanted by accessing a vein with a needle, attaching a filter wire dispenser storing a length of filter wire to the needle, and advancing the filter wire through the needle such that the filter wire exists the delivery end of the needle. In one or more embodiments, the filter wire has two ends, a first end and a second end. In one embodiment the first end of the filter wire exits the dispenser first. As the filter wire exits the needle into the vein, it begins to coil, as described above, to form a vascular filter.

Once the vascular filter is fully deployed the needle may be removed. In one or more embodiments, a portion of the filter wire is left protruding out of the patient so that it may be secured to a fixation device which generally covers the exist passage of the filter wire.

In some embodiments, proper access to a vein may be verified prior to implanting the filter. One way to verify that the needle is accurately located in a vein is to attach a syringe to the needle and draw blood from the vein to confirm the needle is indeed properly within the vein. The needle is improperly placed if no blood can be drawn. Once verified, the syringe may be removed from the needle while leaving the needle in the vein. A filter wire dispenser may then be attached and the filter wire implanted subsequently.

The vascular filter may be removed when desired or when no longer needed. In one embodiment, the vascular filter is removed by removing the filter wire from its associated fixation device and drawing the filter wire out of the patient. As the filter wire is drawn out of the patient, the filter wire unwinds itself so that it may be easily removed.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF THE PREFERRED EMBODIMENTS

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

One of the primary concerns regarding deep vein thrombosis (DVT) is that should the thrombosis (blood clot) dislodge from the original location, the clot may travel to another region of the circulatory system and cause injury and or death to the subject. For example, if a DVT dislodges it may migrate through the heart and eventually re-lodge in the lung of the subject thus causing a pulmonary embolism (PE) which prevents adequate circulation and can cause sudden death. By placing an intravenous filter in the common femoral vein, the blood clot is captured and prevented from migrating to vulnerable regions of the circulatory system. The filter may be placed in any vein or at any location such that the filter can capture a clot prior to causing damage to the patient. The term vein and vessel are used and defined interchangeable herein.

Figure 1:
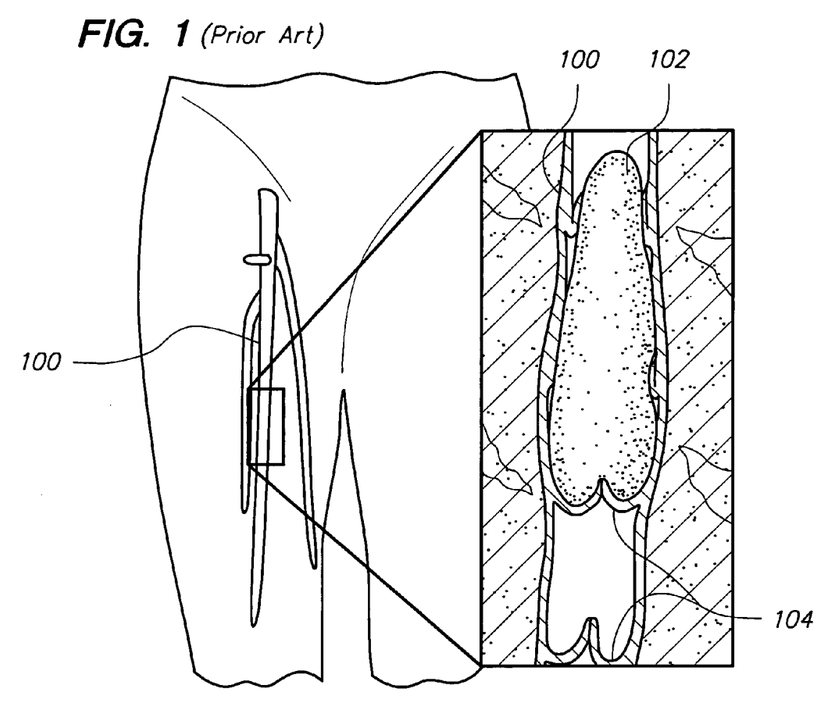
FIG. 1 illustrates a typical blood clot lodged within a femoral vein.

Referring now to the drawings, FIG. 1 illustrates a typical DVT where the common femoral vein 100 has a blood clot 102 lodged therein. As the blood clot 102 is formed there is reduced blood flow through the common femoral vein 100 because the blood clot begins to obstruct the fluid pathway. The reduced blood flow produces an environment that facilitates clot formation. In particular, as the blood flow is reduced, blood begins to coagulate in the chambers of the vascular valves 104 and as a result the blood clot 102 increases in size.

Figure 2:
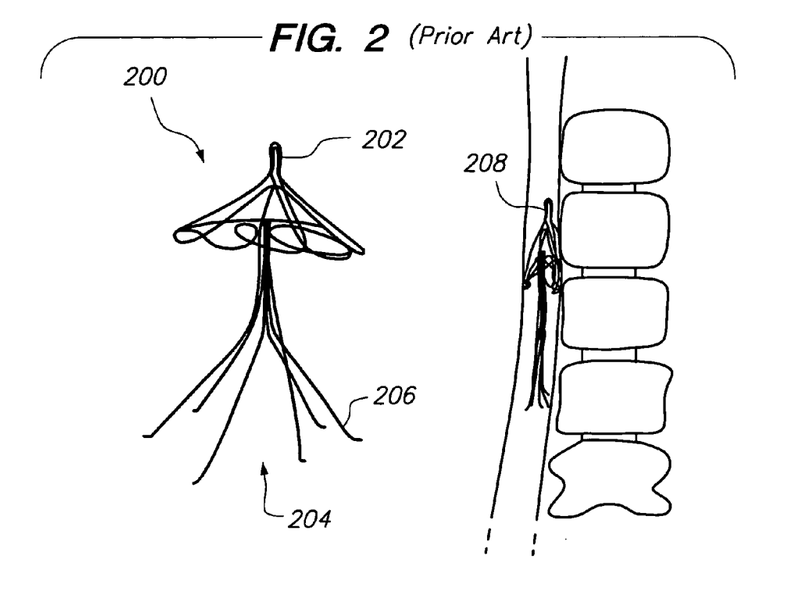
FIG. 2 illustrates an existing inferior vena cava filter and the proximate location of the filter in the upper abdomen.

FIG. 2 illustrates a known inferior vena cava vascular filter that is surgically implanted into the patient's upper abdomen. This inferior vena cava filter (IVC filter) 200 is commonly deployed using a large bore catheter and access to a large bore vein such as the inferior vena cava. The IVC filter 200 has a first end 202 and a second end 204 where the second end comprises a plurality of individual wire components 206. In the proximity diagram of FIG. 2, an IVC filter 200 is shown within the inferior vena cava at location 208 in the upper abdomen of a patient.

Figure 3:
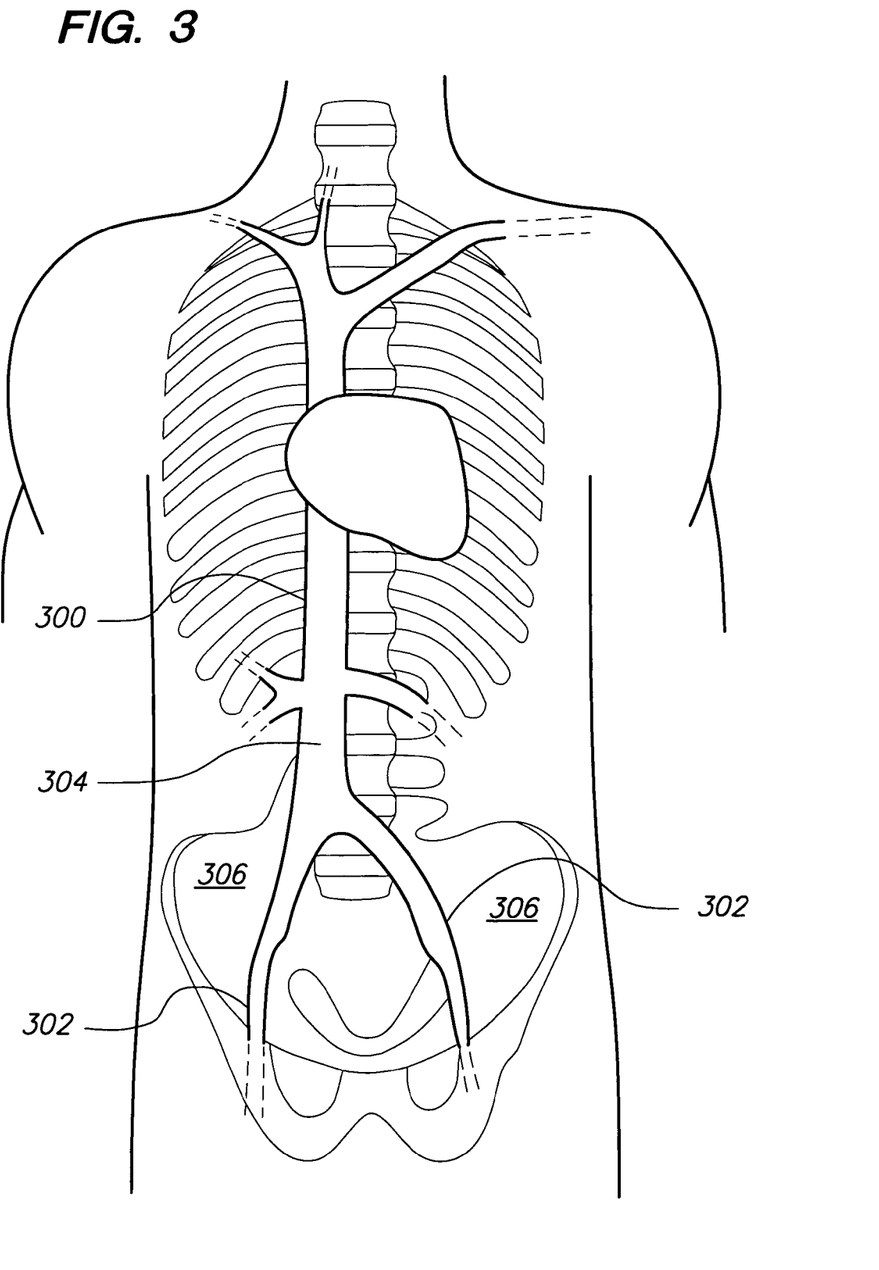
FIG. 3 illustrates the inferior vena cava and the two femoral veins.

FIG. 3 illustrates the inferior vena cava 300 and two common femoral veins 302 branching off the inferior vena cava. In the known use of intravenous filters such as the IVC filter discussed above, it is common to place the IVC filter within the inferior vena cava 300 at location 304 in the upper abdomen.

As stated above, placement of an IVC filter within the inferior vena cava 300 is expensive, requires special surgical procedures, requires imaging from a radiology or cardiology suite to ensure correct placement with the inferior vena cava, and is a substantially difficult and complicated surgery. In addition, known IVC filters must be placed in a large bore vein, and the placement surgery itself poses a significant risk in patients with conditions that prevent proper blood clotting.

The vascular filter of the present invention has several advantages over known filters. In contrast to the above, the vascular filter of the present invention may be placed within one of the common femoral veins 302. In addition, the vascular filter may be placed at any other location in the body which is suited to capture or retain blood clots. The vascular filter may be placed "blind" without imaging guidance from an expensive radiology or cardiology suite. Furthermore, the vascular filter may be placed in the common femoral vein 302 at hip level which is an area routinely used for catheter and other line access. Use of this common access area is another advantage in that such use of a commonly accessed area tends to reduce complexity and risk during placement as it is a well known access area.

Though placement at hip level has advantages, placement at hip level may not be ideal in all patients and thus the vascular filter may also be placed in other areas. For example, in one embodiment, the filter may be placed in the groin region 306 of the patient. It is contemplated that the vascular filter of the present invention may be placed where it is best able to capture a dislodged blood clot and that more than one filter may be placed to ensure that any dislodged blood clots are captured. For example, in one embodiment the vascular filter may be placed in both of the common femoral veins 302 should the patient's medical condition require filtration of both legs. In other embodiments, additional vascular filters may be placed as well.

Placement of the vascular filter begins by accessing a common femoral vein 302. Though the following description describes an embodiment of the present invention where the vascular filter is placed within a common femoral vein 302, the vascular filter may be similarly placed in other veins where dislodged blood clots may be captured as necessary.

Figure 4:
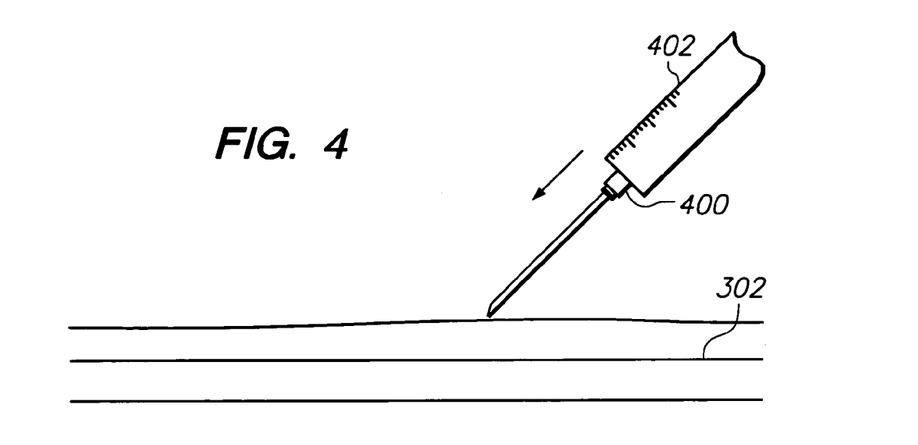
FIG. 4 illustrates a common femoral vein prior to access by a needle and syringe assembly.
Figure 5:
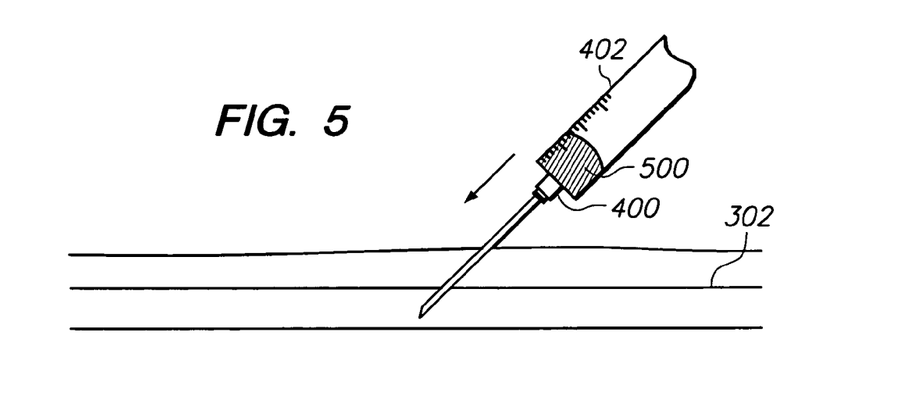
FIG. 5 illustrates actual needle and syringe assembly access into the common femoral vein.

FIGS. 4 and 5 illustrate a common femoral vein 302 accessed by a dispensing needle 400 and syringe 402 assembly. In one or more embodiments, the needle 400 has a first or delivery end through which a vascular filter is implanted in a patient, and a second or coupling end at which a syringe or filter dispenser may be attached. Notably, the coupling end in one or more embodiments may be configured to permit releasable attachment of the needle 400 as described further below.

Generally, proper access to the common femoral vein 302 may be verified by syringe aspiration (drawing blood from the vein into the body of the syringe) and is visually confirmed by blood return 500 into the syringe. In other embodiments, elements other than a syringe may be utilized including, but not limited to a single hollow large bore needle of which the blood can be seen flowing out of without syringe aspiration.

Figure 6:
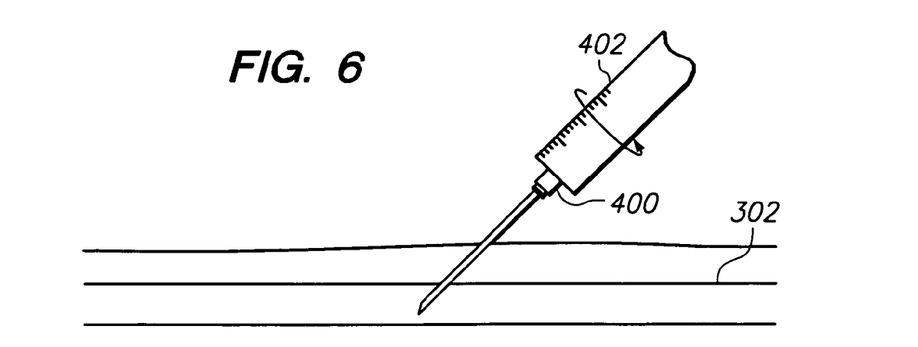
FIG. 6 illustrates removal of the syringe.

As illustrated in FIG. 6, the syringe 402 may be disengaged or removed from the needle 400 without removing the needle from the common femoral vein 302. In one or more embodiments, proper access to the common femoral vein 302 may be confirmed prior to disengaging the syringe 402 by inspecting the syringe for blood return. Such blood return confirms that the needle 400 is within a vein.

It is noted that disengagement or removal of the syringe 402 from the needle 400 may occur in various ways and that the syringe is releasably attached to the needle. For example, the syringe 402 may be fitted with a bayonet type of locking mechanism that retains the needle 400 within the end of the syringe. In addition, any other type of mechanism in addition to or other than a bayonet type locking mechanism may be utilized including but not limited to a manufactured threaded coupling system with "male and female" thread components. The locking mechanism may be any type of configuration that releasably retains the needle in the syringe and because these mechanisms are well known in the art they will not be described in detail so as not to obscure the present invention.

Figure 7:
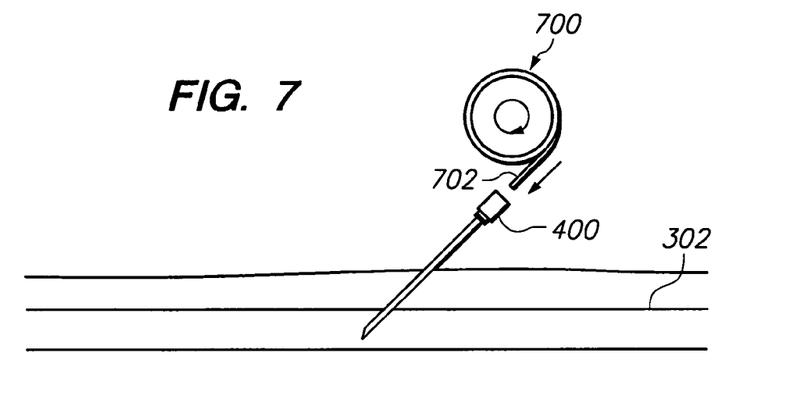
FIG. 7 illustrates attachment of the filter dispenser to the needle.

Attachment of the vascular filter dispenser 700 to the needle 400 is illustrated in FIG. 7. In one embodiment, the vascular filter dispenser 700 is a spool device that is configured to house and dispense filter wire housed with in the dispenser. The vascular filter dispenser 700 is fitted with a guide tube 702 that facilitates the deployment of the filter wire from the dispenser through the needle 400 and into the common femoral vein 302. It is contemplated that the end of the guide tube 702 be sized for operative insertion into the inner diameter of the needle 400. The guide tube 702 provides a smooth transition for the filter wire during the deployment process as the wire leaves the filter dispenser 700 and enters the needle 400. In some embodiments, filter means other than a wire may be utilized such as but not limited to monofilament strand or other materials with reformable properties. These structures may be preformed or shaped and/or configured at the time of use.

Figure 8:
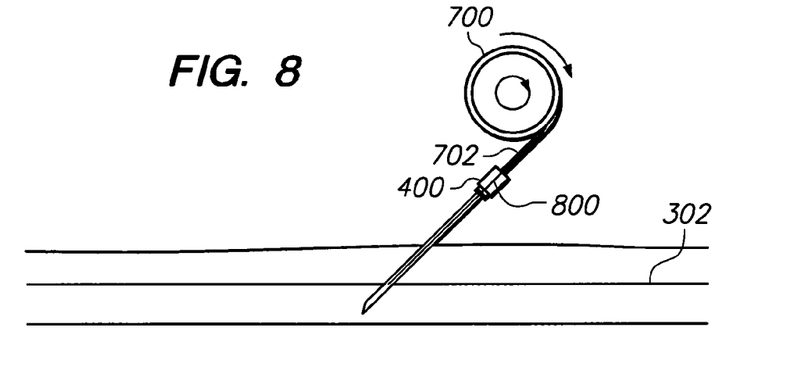
FIGS. 8 through 11 illustrate deployment of the vascular filter.

Reference is now made to FIGS. 8 through 11 individually and in combination for illustrating the deployment of the vascular filter. As shown in FIG. 8, a needle 400 and a vascular filter dispenser 700 are coupled together and the filter dispenser is actuated such that the filter wire 800 is fed from the dispenser through the needle and into the common femoral vein 302. In one embodiment, the filter dispenser 700 is actuated by a rotational movement of the dispenser so that the filter wire 800 is uncoiled and fed down the guide tube 702 and into the needle 400. It is contemplated that the filter dispenser 700 may comprise a user-rotatable wheel or knob in one or more embodiments. When rotated, the knob un-coils the filter wire 800 and feeds the same down the guide tube 702. The knob may un-coil the filter wire 800 through physical contact with the filter wire. However, it is contemplated that there may be an attached reel which is actuated by rotational movement of knob. Other embodiments of the filter dispenser 700 are contemplated such as a linear dispenser by which the filter wire is translated down the length of the dispenser and into the needle.

Figure 9:
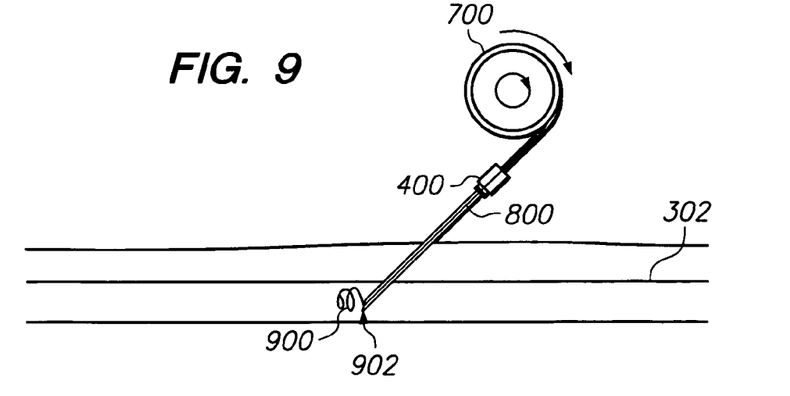

As best illustrated in FIG. 9, as the filter wire 800 traverses down the needle 400 it remains substantially straight. However, when the filter wire 800 exits the end of the needle 902, the filter wire begins to form a coil 900 within the common femoral vein 302. The filter wire coils due to residual stresses of the wire and the preformed shape memory imparted into the wire during the manufacturing process.

In one or more embodiments, the filter wire 800 has a first and a second end and is preferably fabricated from a suitable material such as titanium, Nitinol, or monofilament strand to name a few. The filter wire 800 may also be fabricated from polymer as well. The wire may be similar to known wires commonly used in the medical industry and, in one or more embodiments, may range in diameter from 0.015-0.035 of an inch. Additionally, the filter wire 800 may be treated with a compound that prevents clot formation on the wire such as a Heparin anticoagulation coating. The wire may comprise a mesh form or may be constructed of metal, plastic or a combination thereof or any other material. In addition, the filter wire 800 may have a very flexible tip at its first end to reduce the possibility of damaging the inside wall of a vein when the filter wire is implanted.

In one embodiment, an important characteristic of the filter wire 800 is that the wire be preformed to have residual stresses and/or surface tensions such that the wire will automatically coil once advanced beyond the delivery needle end 902. For example, the filter wire may be fabricated so that the surface tension along the length of the wire causes the wire to naturally coil unless otherwise constrained. In this way, the filter wire 800 may be housed or stored in one dispenser configuration and upon proper deployment; the filter wire would coil into a predetermined shape. In another embodiment, the filter wire may be preformed to take any various shapes that will achieve the goals set forth herein. For example, the filter wire may be preformed to have a vortex shape (coils of increasing/decreasing diameter) once deployed. Other embodiments may provide filter wire that is preformed to have a nesting or tangled web shape.

Figure 10:
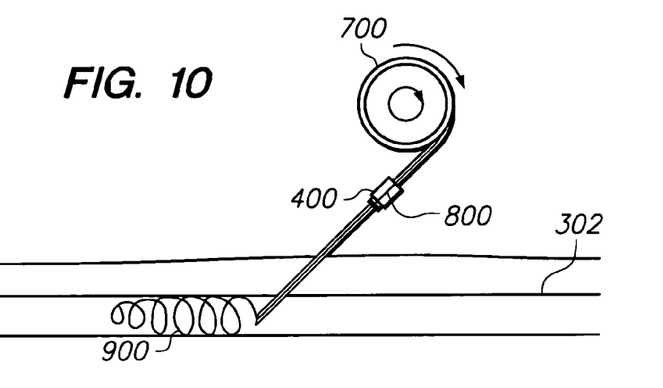
Figure 11:
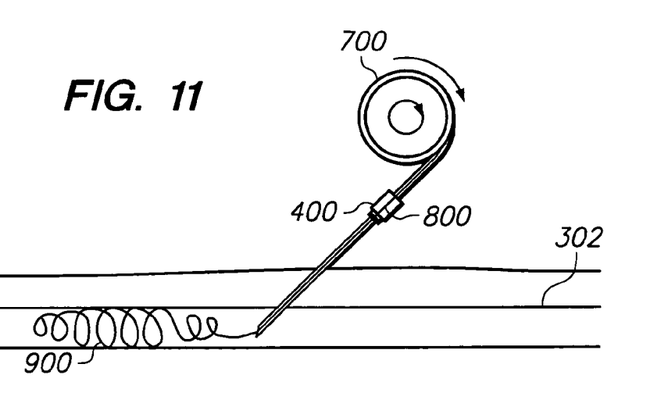

As illustrated in FIGS. 10 and 11, as the filter wire 800 is advanced into the common femoral vein 302, the coil becomes larger and longer such that a substantial coil of wire is formed within the vein. As a result, the coil 900 becomes a partial flow restriction within the common femoral vein 302 capable of capturing and retaining a blood clot therein.

Figure 12:
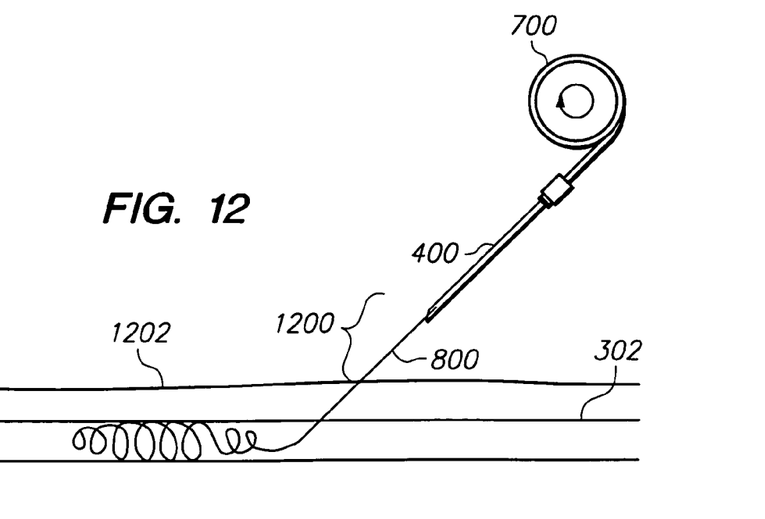
FIGS. 12 and 13 illustrate removal of the filter dispenser and needle.
Figure 13:
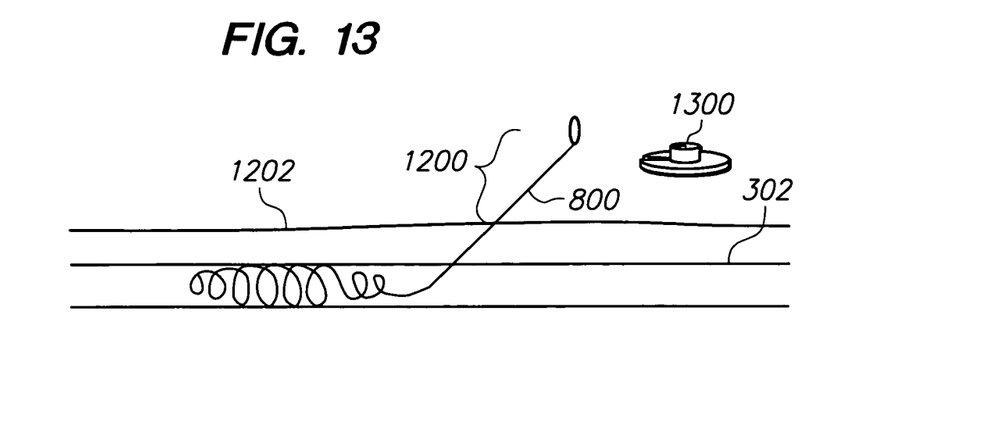
Figure 14:
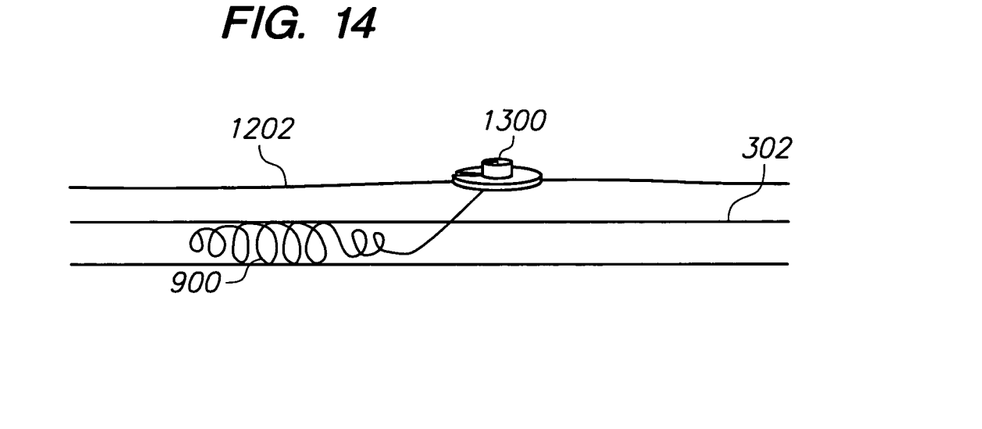
FIG. 14 illustrates retention of the filter wire to the patient's leg.

In FIG. 12, the filter wire 800 has been deployed and the filter dispenser 700 and delivery needle 400 are retracted from the subject's common femoral vein 302. As the dispenser 700 and needle 400 are removed, a portion 1200 of the filter wire 800 may be left protruding from the subject's skin surface 1202 so that it may be secured to a fixation device 1300 to prevent the filter wire 800 from moving within the vein. As illustrated in FIGS. 13 and 14, a portion 1200 of the filter wire 800 is intentionally left protruding from the subject's skin surface 1202 so that it may be looped and subsequently attached to a fixation device 1300. The fixation device 1300 is then secured using a medical dressing to the subject's skin 1202 and may cover the filter wire's exit. It is contemplated that types of fixation devices 1300 other than those illustrated in the figures may be used, and that in other embodiments the protruding portion 1200 of the filter wire 800 may be attached in other ways such as by tying or adhering the filter wire to the fixation device.

Figure 15:
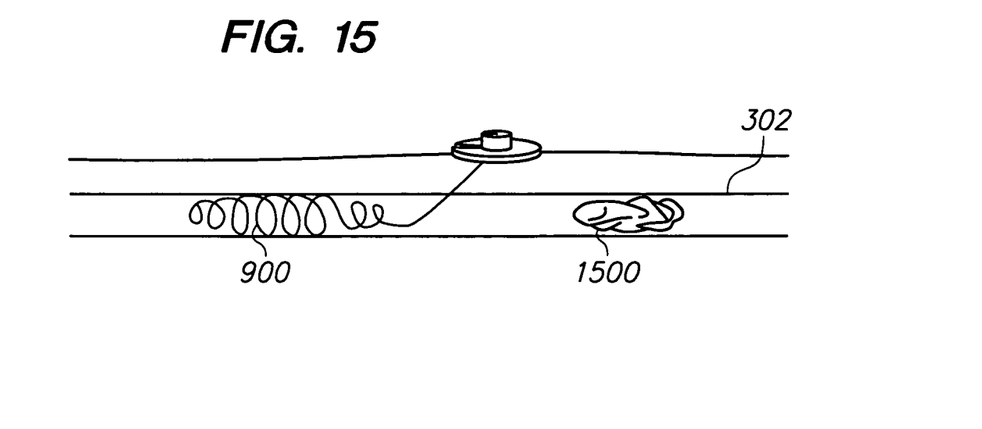
FIG. 15 illustrates a blood clot approaching the deployed vascular filter.
Figure 16:
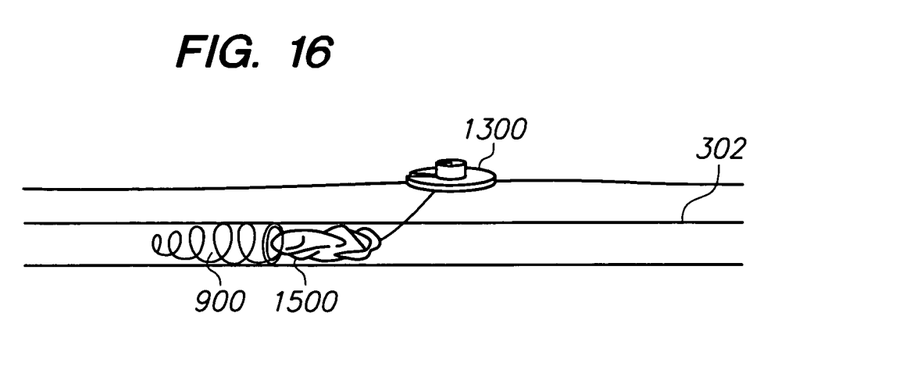
FIG. 16 illustrates the blood clot of FIG. 15 trapped by the vascular filter.

FIGS. 15 and 16 illustrate a blood clot 1500 approaching and being captured by the deployed vascular filter. As the blood clot 1500 migrates down the vein, it will encounter and preferably become trapped by the coil 900 of the vascular filter. As illustrated in FIG. 16, the blood clot 1500 will become lodged or entangled with the vascular filter's coils and in this way the clot is prevented from entering other regions of the subject's circulatory system.

In the event that a blood clot 1500 is captured by the vascular filter, the clot may be removed in one of several ways. First, the entangled blood clot 1500 may be verified using ultrasound or x-ray techniques. If there is a blood clot 1500, then the blood clot may be dissolved using anticoagulation therapy or any other means. If the blood clot 1500 does not dissolve in a timely manner, the attending physician may decide to perform additional procedures such as thrombectomy or thrombolysis to resolve the blood clot. In some cases, permanent placement of a standard IVC filter may be required where the blood clot does not dissolve.

Figure 17:
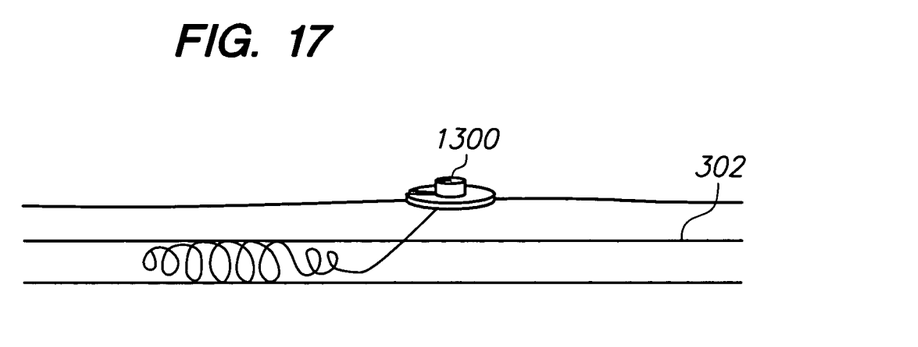
FIGS. 17 through 19 illustrate removal of the vascular filter.
Figure 18A:
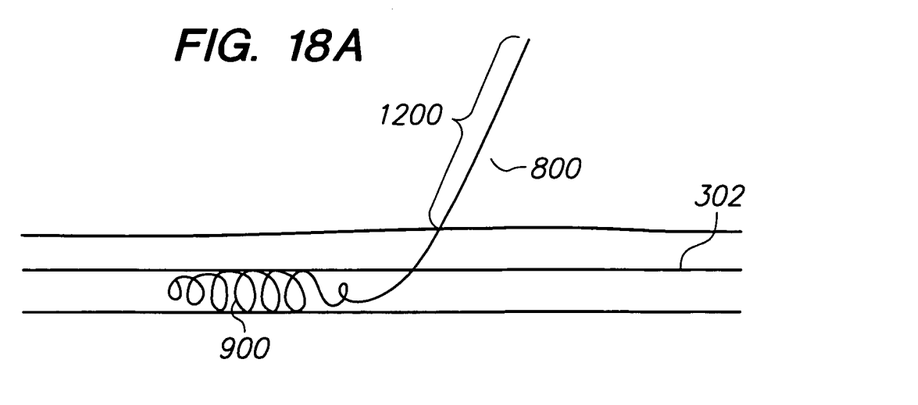
Figure 18B:
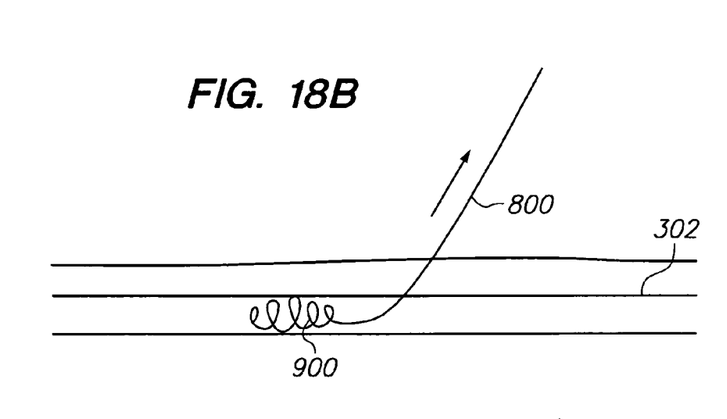
Figure 18C:
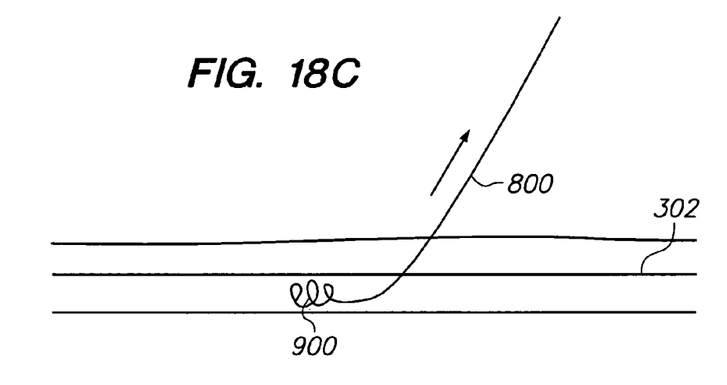
Figure 18D:
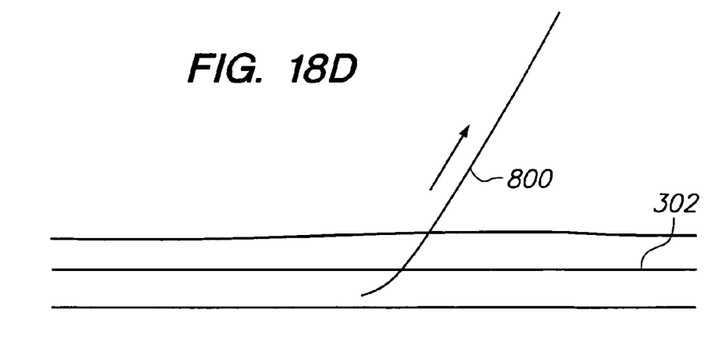
Figure 19:
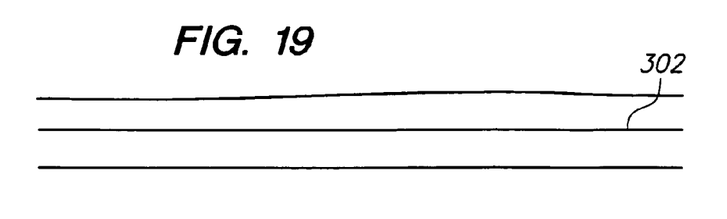

FIGS. 17 through 19 illustrate removal of the vascular filter. In FIG. 17, the fixation device 1300 and associated dressing are removed from the patient's skin surface 1202. Next, the protruding portion 1200 of the filter wire 800 is drawn away from the patient. As the filter wire 800 is drawn out of the patient, the filter coil 900 unwinds and/or unravels as illustrated in FIGS. 18a through 18d. A hydrophilic coating or hydrophilic filter wires 800 may be used, in one or more embodiments, to facilitate removal of the filter coil 900. Once the filter wire 800 is completely extracted from the patient as shown in FIG. 19, the vascular filter has been successfully removed and may be discarded.

The vascular filter disclosed herein has several advantages over known IVC filters. The new vascular filter is inexpensive and easily deployed/removed with minimal intrusion into the patient. In contrast, existing vascular filters require a complex and potentially risky deployment procedure which is very expensive, requires a team of medical professionals and the use of an operating room or cardiology suite. Additionally, existing vascular filters require an even more complicated and risky procedure for removal.

The new vascular filter is placed without the need for complex fluoroscopic guidance (i.e., the new filter is placed blindly). For example, unlike exiting filters that are placed within the inferior vena cava which requires x-ray fluoroscopic guidance for deployment, the new vascular filter may be placed without using any x-ray or imaging equipment.

The new vascular filter is minimally invasive and can be deployed at the patient's bedside or in an emergency room setting. Correspondingly, removal of the new vascular filter may be performed at a convenient location such as bedside.

The new vascular filter reduces the risk of complications because the filter is placed in a more conducive location within the patient's body. As disclosed herein, the new vascular filter may be placed in the pelvic or groin region of the patient unlike existing IVC filters which are generally placed in the upper abdomen or thoracic region. As a result, the new vascular filer is placed within one or both of the more accessible common femoral veins and is minimally intrusive for the patient. Another desirable aspect of the new vascular filter is a substantial reduction in recovery time for either deployment or removal of the new filter. In contrast, the existing filters require a substantial recovery time for both deployment and removal.

While various embodiments of the invention have been described, it will be apparent to those of ordinary skill in the art that many more embodiments and implementations are possible that are within the scope of this invention. In addition, the various features, elements, and embodiments described herein may be claimed or combined in any configuration or arrangement.

What is claimed is:
1. A vascular filter system comprising:
   a dispensing needle having a delivery end and a filter wire dispenser connection end;
   a filter consisting of:
      a length of filter wire having residual stresses, surface tensions, or both that cause the filter wire when deployed in the vein to form a plurality of loops in a helix shape having a center axis that is generally parallel to a direction of the vein;
      wherein the helix shape has proximal, middle, and distal sections; and
      wherein the diameter of the filter at the proximal and distal sections is less than the diameter of the filter at the middle section; and
   a filter wire dispenser for storing a length of filter wire, wherein the filter wire dispenser comprises a guide tube and a spool having a user rotatable wheel or knob, the guide tube sized for connection to the filter wire dispenser connection end of the dispensing needle; and the filter wire being configured to (i) coil within or around the spool (ii) deploy from the filter wire dispenser to a vein of a patient, thereby filtering the vein, and (iii) completely retract percutaneously from the vein after filtering blood flow in the vein.

2. The vascular filter system of claim 1, wherein the filter wire has a first end portion with a rounded tip that is more flexible than other portions of the wire.

3. The vascular filter system of claim 1 further comprising a fixation device configured to attach to a patient and to a portion of the filter wire to thereby secure the filter wire.

4. A vascular filter system comprising:
a dispensing needle, the dispensing needle having a delivery end and a coupling end;
a filter consisting of:
a length of filter wire, the filter wire having residual stresses, surface tensions, or both that cause the filter wire to form a conical coil having proximal, middle, and distal sections upon deployment from the delivery end of the needle;
a filter wire dispenser for storing the length of filter wire, the filter wire dispenser having:
a storage housing having a spool configured to store the filter wire wrapped around the spool prior to dispensing in a patient;
a user rotatable wheel or knob;
a coupling end configured to releasably attach to the coupling end of the dispensing needle;
a guide tube between the storage housing and the coupling end configured to guide the filter wire from the storage housing to the coupling end,
the coupling end of the dispensing needle being releasably connectable to a syringe, the syringe configured to be maneuverable to insert the dispensing needle into a vein of the patient and configured to draw blood into the syringe to detected placement of the dispensing needle into the vein, and the coupling end of the dispensing needle also releasably connectable to the coupling end of the filter wire dispenser while the dispensing needle is inserted in the vein of the patient.

5. The vascular filter system of claim 4, further comprising a fixation device configured to attach to a portion of the filter wire which protrudes from the patient when in use.

6. A vascular filter system comprising:
a filter consisting of: a wire comprising a resilient material, the resiliency causing the filter wire, upon delivery into a vessel, to form a helix shape with proximal, middle, and distal sections and a central axis that is generally parallel to a central axis of the vein;
wherein a diameter of the filter at the proximal and distal sections is less than a diameter of the filter at the middle section;
a filter dispenser comprising a guide tube for guiding the filter wire into the vessel of a patient, the filter wire stored within a reel mechanism of the filter dispenser;
a dispensing needle having a proximal end coupled to the guide tube and a pointed distal end and a channel therethrough for accepting the filter wire; and
the reel mechanism configured to be rotatable by a user to store the filter wire and push the filter wire through the guide tube and dispensing needle and into the vessel,
the dispensing needle being configured to be removable from the vessel while the filter wire is disposed both in the vessel and within the channel, and
the filter wire being configured to percutaneously extend into the vessel to filter the vessel and to be percutaneously removable from the vessel after filtering blood flow in the vessel.

7. The vascular filter system of claim 6, wherein the dispensing needle is removable from the guide tube.

8. The vascular filter system of claim 6, further comprising a coupler at the guide tube to engage one or more replacement dispensing needles.

9. The vascular filter system of claim 6, further comprising a fixation device configured to attach to a portion of the filter wire which protrudes from the patient when in use.

10. The vascular filter system of claim 6, further comprising a fixation device configured to attach a portion of the filter wire which protrudes from the patient to the patient's skin.

\* \* \* \* \*